(12) United States Patent
Miyoshi

(10) Patent No.: US 8,187,173 B2
(45) Date of Patent: May 29, 2012

(54) APPARATUS FOR ADVANCING AN ENDOSCOPE AND METHOD FOR MANIPULATING THE APPARATUS FOR ADVANCING AN ENDOSCOPE

(75) Inventor: Hiroaki Miyoshi, Fuchu (JP)

(73) Assignee: Olympus Medical Systems Corp., Tokyo (JP)

( * ) Notice: Subject to any disclaimer, the term of this patent is extended or adjusted under 35 U.S.C. 154(b) by 976 days.

(21) Appl. No.: 12/174,119

(22) Filed: Jul. 16, 2008

(65) Prior Publication Data

US 2009/0062608 A1   Mar. 5, 2009

(30) Foreign Application Priority Data

Aug. 28, 2007   (JP) .................... 2007-221687

(51) Int. Cl.
*A61B 1/00*   (2006.01)
(52) U.S. Cl. .............. 600/115; 600/114; 604/101.01; 604/101.04; 604/101.05
(58) Field of Classification Search .......... 600/115–116; 604/101.01–101.05
See application file for complete search history.

(56) References Cited

U.S. PATENT DOCUMENTS

| | | | | |
|---|---|---|---|---|
| 4,040,413 A * | 8/1977 | Ohshiro | .................. | 600/116 |
| 5,090,959 A * | 2/1992 | Samson et al. | .................. | 600/116 |
| 5,160,321 A * | 11/1992 | Sahota | .................. | 604/101.03 |
| 5,320,605 A * | 6/1994 | Sahota | .................. | 604/101.01 |
| 5,658,311 A * | 8/1997 | Baden | .................. | 606/192 |
| 5,669,924 A * | 9/1997 | Shaknovich | .................. | 623/1.11 |
| 2006/0025654 A1 * | 2/2006 | Suzuki et al. | .................. | 600/114 |
| 2007/0078302 A1 * | 4/2007 | Ortiz et al. | .................. | 600/115 |
| 2007/0083082 A1 * | 4/2007 | Kiser et al. | .................. | 600/115 |
| 2008/0161645 A1 * | 7/2008 | Goldwasser et al. | .................. | 600/115 |

FOREIGN PATENT DOCUMENTS

| | | |
|---|---|---|
| JP | 2000-033071 A | 2/2000 |
| JP | 2002-065595 | 3/2002 |
| JP | 2002-301019 | 10/2002 |

OTHER PUBLICATIONS

Japanese Office Action dated Mar. 21, 2012 in counterpart Japanese Patent Application No. 2007-221687.

* cited by examiner

*Primary Examiner* — Matthew J Kasztejna
(74) *Attorney, Agent, or Firm* — Scully, Scott, Murphy & Presser, PC

(57) ABSTRACT

In a region where an intestine is movable in the abdominal cavity, conventional endoscope apparatus have suffered from a difficulty in moving an endoscope advancing portion toward a deep intestinal portion. An apparatus for advancing an endoscope is provided, which can be easily manipulated to advance medical instruments having endoscopic functions toward a deep portion. The apparatus includes first and second medical instruments, each having, at a distal end portion thereof, a balloon portion that can be fixed to an intestinal wall. In a fixed state, the balloon portion of the first medical instrument is configured to form a gap for enabling a distal end portion of the second medical instrument to advance therethrough. In a fixed state, the balloon portion of the second medical instrument is configured to form a gap for enabling a distal end portion of the first medical instrument to advance therethrough.

13 Claims, 15 Drawing Sheets

APPARATUS FOR ADVANCING AN ENDOSCOPE AND METHOD FOR MANIPULATING THE APPARATUS FOR ADVANCING AN ENDOSCOPE

CROSS REFERENCE TO RELATED APPLICATION

This application claims the benefit of Japanese Application No. 2007-221687 filed in Japan on Aug. 28, 2007, the contents of which are incorporated herein by this reference.

BACKGROUND OF THE INVENTION

1. Field of the Invention

The present invention relates to an apparatus for advancing an endoscope and a method for manipulating the apparatus for advancing an endoscope. In particular, the present invention relates to an apparatus for advancing an endoscope, having a plurality of medical instruments, each of which is provided with a fixing portion that can achieve fixation to an intestinal wall, and relates to a method for manipulating the apparatus for advancing an endoscope.

2. Description of the Related Art

Generally, an endoscope includes a flexible portion which is an elongated tube having flexibility, a bending portion which is connected to a distal end portion of the flexible portion and can be manipulated by an operation portion for bending in the horizontal or/and vertical directions, and a rigid distal end portion which is connected to a distal end portion of the bending portion. Such an endoscope is adapted to be inserted into a body cavity anally, orally or nasally to conduct, for example, observation and diagnosis of a predetermined region, or conduct treatment while the region is observed.

However, the insertion of such a conventional endoscope into a deep digestive tract, such as a small intestine, via a large intestine has been accompanied by a difficulty. Specifically, due to the complicated bending of the intestinal tract, simply pressing the endoscope into the body cavity hardly permits transmission of a force to the end of the endoscope, and thus advancement into a deep portion has been difficult. For this reason, the technique of advancing a large intestine endoscope has required some manipulations, such as angle adjusting, twisting, pulling back and axis retaining manipulations, or has additionally required air supply and x-ray fluoroscopy, for example.

In order to facilitate the manipulations mentioned above, an endoscope having fixing balloons as described below has been suggested.

For example, Japanese Patent Application Laid-Open Publication No. 2002-65595 discloses a multi-stage tube with balloons, wherein two tubes are formed, each of the tubes including: a balloon portion which is provided near an end of the tube, and is inflatable/shrinkable by means of fluid; a fluid channel which is provided in a tube wall and communicates with the balloon portion; and a fluid supply device which is provided at a proximal end portion of the tube and communicates with the fluid channel.

Also, Japanese Patent Application Laid-Open Publication No. 2002-301019 discloses an endoscope including: an endoscope body provided with a balloon at an outer end peripheral portion thereof, for fixation of the body; and a sliding tube which is provided with a balloon for fixation of the tube at the outer end peripheral portion thereof and into which the endoscope body is inserted to guide the endoscope body.

FIGS. 29A to 29H are explanatory views illustrating a procedure for inserting into a large intestine the double-balloon type endoscope disclosed in Japanese Patent Application Laid-Open Publication No. 2002-65595. In the double-balloon type endoscope, the balloons 30a and 30b respectively attached to the over tube 40a and the end of the endoscope body fix the medical instrument (endoscope body) 2a and the over tube 40a to an intestine. Thus, with the procedure sequentially shown in FIGS. 29A to 29H, the balloons 30a and 30b are alternately fixed to the intestine to have an endoscope 2c advanced to the side of a deep portion. The over tube 40a then catches up with the endoscope by the amount of advancement. Reiterating these manipulations can allow the endoscope 2c to tug the intestine and reach a deep portion of the large intestine or the small intestine.

SUMMARY OF THE INVENTION

In order to achieve the above object, an apparatus for advancing an endoscope of the present invention including a first medical instrument and a second medical instrument, is so configured that: each of the first medical instrument and the second medical instrument includes a fixing portion at a distal end portion thereof for fixation to an intestinal wall; the fixing portion provided at the first medical instrument is configured to form a gap in the state of being fixed to the intestinal wall, which enables the distal end portion of the second medical instrument to advance therethrough; and the fixing portion provided at the second medical instrument is configured to form a gap in the state of being fixed to the intestinal wall, which enables the distal end portion of the first medical instrument to advance therethrough.

BRIEF DESCRIPTION OF THE DRAWINGS

FIGS. 7A and 713 are explanatory views each illustrating a mating projection according to a second modification of the first embodiment;

DETAILED DESCRIPTION OF THE PREFERRED EMBODIMENTS

First Embodiment

With reference to the drawings, hereinafter will be described an apparatus for advancing an endoscope according to a first embodiment of the present invention.

Figure 1:
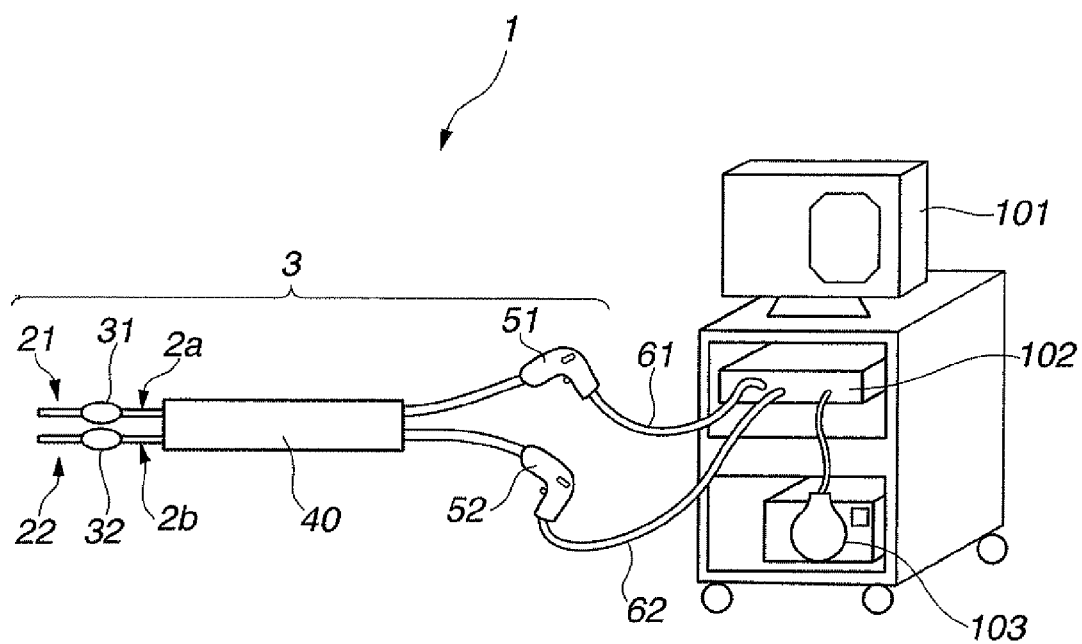
FIG. 1 is a schematic view generally illustrating an endoscope apparatus provided with an apparatus for advancing an endoscope according to a first embodiment of the present invention.
Figure 3:
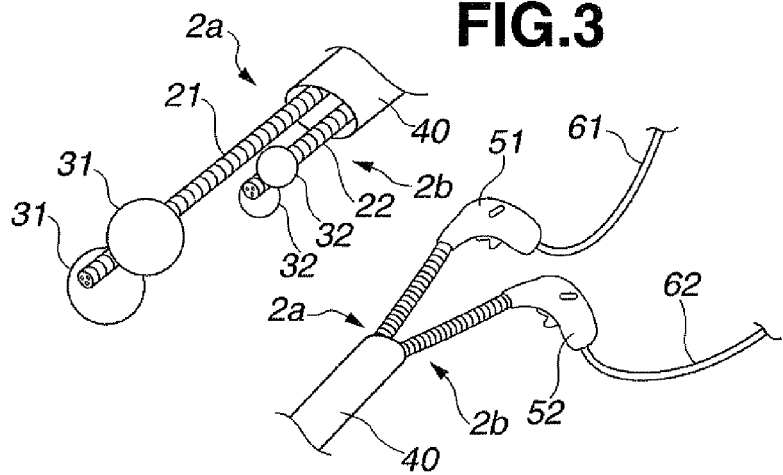
FIG. 3 is an outline view illustrating the apparatus for advancing an endoscope according to the first embodiment.

FIG. 1 is a schematic view generally illustrating an endoscope apparatus 1 having an apparatus 3 for advancing an endoscope according to the first embodiment of the present invention. FIG. 3 is an outline view of the apparatus 3 for advancing an endoscope according to the first embodiment of the present invention.

The endoscope apparatus 1 is provided with the apparatus 3 for advancing an endoscope which includes two medical instruments 2a and 2b to be inserted into a patient's body, operation portions 51 and 52 for independently manipulating the medical instruments 2a and 2b, respectively, and connecting cords 61 and 62. The endoscope apparatus 1 is also provided, for example, with a processor 102 including circuits and the like for controlling the functions loaded on the apparatus 3 for advancing an endoscope and processing image signals picked up by the apparatus 3 for advancing an endoscope, a monitor 101 for displaying the image picked up by the apparatus 3 for advancing an endoscope, and a pump 103 for supplying air and water to the large intestine and sucking fluid and gas from the large intestine, through the apparatus 3 for advancing an endoscope.

The medical instruments 2a and 2b as well as the operation portions 51 and 52 are integrally configured. The medical instruments 2a and 2b are individually provided with inflatable/shrinkable balloon portions 31 and 32 for serving as fixing portions to an intestine, respectively, at distal end portions 21 and 22 of the medical instruments, and are bundled by a sheath 40.

Figure 2:
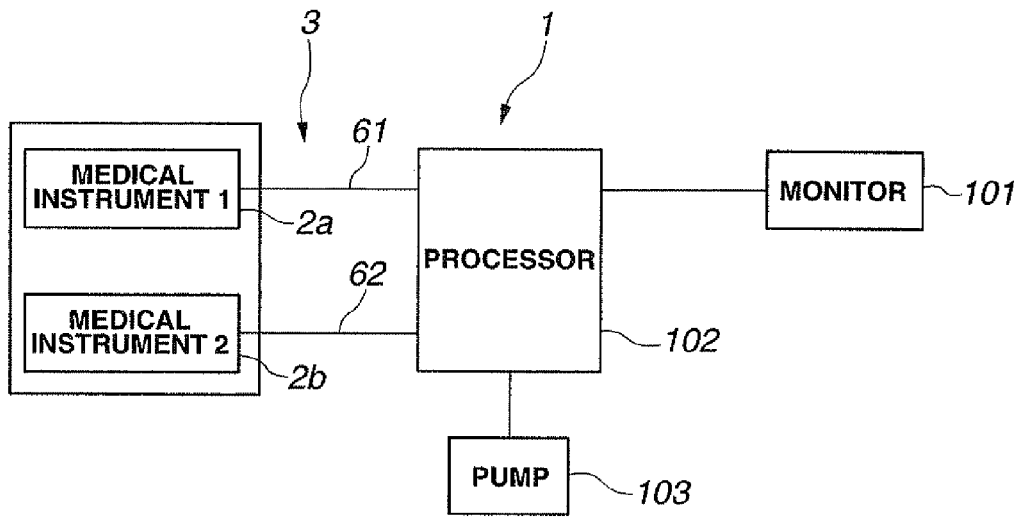
FIG. 2 is a block diagram illustrating connection of an endoscope apparatus having the apparatus for advancing an endoscope according to the first embodiment.

FIG. 2 is a block diagram illustrating connection of the endoscope apparatus 1 having the apparatus 3 for advancing an endoscope according to the first embodiment. The apparatus 3 for advancing an endoscope is detachably connected to the processor 102. In order to prevent the intestine from being punched by an over-inflated balloon, the pump 103 is connected to the processor 102 and put under the control of the processor 102, so that the pressure applied to the balloons by the pump 103 does not exceed a predetermined level.

The apparatus 3 for advancing an endoscope of the first embodiment includes: the first medical instrument 2a and the second medical instrument 2b; and the balloon portion 31 serving as a first fixing portion and the balloon portion 32 serving as a second fixing portion, which are located in the vicinities of the distal end portions 21 and 22, respectively, of the medical instruments. Briefly, in the first embodiment, the fixing portions correspond to balloon portions which can be inflated/shrunk by a gas. Each of the balloon portions 31 and 32 includes two balloons. The sheath 40 plays a roll of bundling the two medical instruments 2a and 2b. Also, the medical instruments 2a and 2b are connected to the processor 102 by means of the connecting cords 61 and 62 through the operation portions 51 and 52.

Figure 4A:
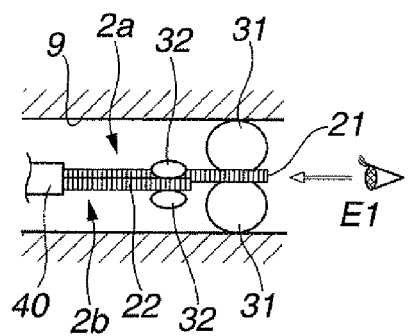
FIGS. 4A and 4B are explanatory views each illustrating a state where the apparatus for advancing an endoscope according to the first embodiment is being inserted into an intestine.
Figure 4B:
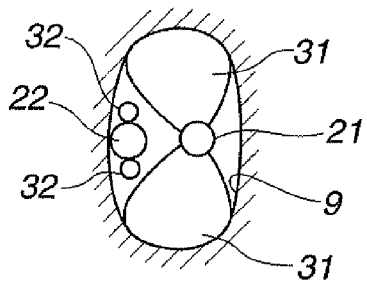

FIGS. 4A to 4B are explanatory views each illustrating a state where the apparatus 3 for advancing an endoscope according to the first embodiment is being inserted into an intestine. FIG. 4A shows a state as viewed from a direction perpendicular to the longitudinal direction of the intestine. FIG. 4B shows a state as viewed from an eyepoint E1 which is on the (right) side of the deep intestinal portion shown in FIG. 4A.

In FIGS. 4A and 4B, the balloon portion 31 at the distal end portion 21 is inflated and fixed to an intestinal wall 9. On the other hand, the balloon portion 32 at the distal end portion 22 is in a shrunk state, not being fixed to the intestinal wall 9. As shown in FIG. 4B, the balloon portion 31, although inflated and fixed, has a notched portion provided at a portion in a peripheral direction of the intestinal wall, to leave a relatively large space between the balloon portion 31 and the intestinal wall 9. In other words, the balloon portion 31 provided at the medical instrument 2a is configured to form a gap when the intestinal wall is pressed, for enabling advancement of the distal end portion 22 of the medical instrument 2b having the balloon portion 32. Or, when the medical instrument 2a is fixed to the intestinal wall by the balloon portion 31, the space formed between the medical instrument 2a and the intestinal wall forms a gap that enables advancement of the distal end portion 22. It should be appreciated that the term "notched portion" of the balloon portion 31 mentioned above refers to a portion between the intestinal wall 9 and the distal end portion 21, which is not occupied by the balloon portion 31, that is, a space having a portion where the balloon portion is not in contact with the intestinal wall 9.

The distal end portion 22 having the shrunk balloon portion 32 can advance toward a deeper intestinal portion passing through the space between the inflated balloon portion 31 and the intestinal wall 9. Briefly, the medical instrument 2b can advance to a portion located deeper than the medical instrument 2a.

Further, although not shown, after advancing the distal end portion 22 toward the a portion located deeper than the distal end portion 21, the balloon portion 32 that is the fixing portion of the distal end portion 22, can be inflated for fixation to the intestinal wall 9, and the balloon portion 31 that is the fixing portion of the distal end portion 21 can be shrunk. Then, a relatively large space is now formed between the balloon portion 32 and the intestinal wall 9. Thus, the distal end portion 21 having the shrunk balloon portion 31 can advance toward a deeper intestinal portion passing through the space between the inflated balloon portion 32 and the intestinal wall 9. Specifically, the state where the balloon portion 32, or the fixing portion, is fixed to the intestinal wall 9, can form a gap between the balloon portion 32 and the intestinal wall 9, so that the distal end portion 21 having the balloon portion 31, or the fixing portion, can pass through the gap.

Referring now to FIGS. 5A to 5H, hereinafter is described a method for manipulating the apparatus for advancing an endoscope, in advancing medical instruments in a large intestine, according to the first embodiment. FIGS. 5A to 5H each illustrate only the balloon portions 31 and 32, and the sheath 40.

(1) FIG. 5A:

The distal end portion 21 having the balloon portion 31 as the first fixing portion, the distal end portion 22 having the balloon portion 32 as the second fixing portion, and the sheath 40 are inserted into an intestinal tract. Upon the insertion, first, the distal end portion 21 is inserted ahead of the distal end portion 22. Then, the balloon portion 31 is inflated for achieving fixation between the intestinal wall 9 and the distal end portion 21.

(2) FIG. 5B:

The intestinal tract is tugged to the side of the anus when the distal end portion 21 is pulled to the side of the anus in the state of being fixed between the intestinal wall 9 and the balloon portion 31. Then, the distal end portion 22 having the balloon portion 32 as the fixing portion for the intestinal wall 9 is advanced, passing through the space between the distal end portion 21 of the balloon portion 31 that has been inserted earlier and the intestine, until the distal end portion 22 reaches a deeper portion. As a matter of course, at this point, the balloon portion 32 is in a state of being shrunk, or in a non-fixing state, and thus is movable.

(3) FIG. 5C:

At the point the distal end portion 22 has reached the deeper portion which is located deeper than the intestinal wall portion to which the distal end portion 21 is fixed, the balloon portion 32 is inflated by a supply of air, for fixation to the intestinal wall 9. Then, the air is discharged from the balloon portion 31 as the fixing portion that has been inserted earlier and located closer to the anus, so that the balloon portion 31 is shrunk to release the fixation between the intestinal wall 9 and the balloon portion 31.

(4) FIG. 5D:

The intestinal tract is tugged to the side of the anus when the distal end portion 22 is pulled to the side of the anus in the state of being fixed between the intestinal wall 9 and the balloon portion 32 at the deeper portion.

(5) FIG. 5E:

The balloon portion 31 whose fixation has been released is advanced, passing through the space between the balloon portion 32 located in the deeper portion and the intestinal wall 9 to reach a further deeper portion.

(6) FIG. 5F:

The balloon portion 31 is inflated to achieve fixation between the intestinal wall 9 and the distal end portion 21. On the other hand, the balloon portion 32 is shrunk to release the fixation between the intestinal wall 9 and the distal end portion 22.

Figure 5A:
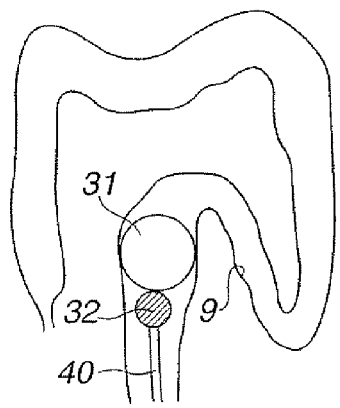
FIGS. 5A to 5H are explanatory views each illustrating a manipulation of the apparatus for advancing an endoscope according to the first embodiment.
Figure 5B:
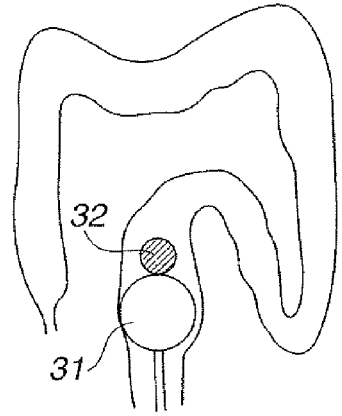
Figure 5C:
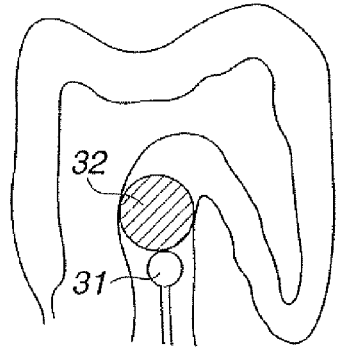
Figure 5D:
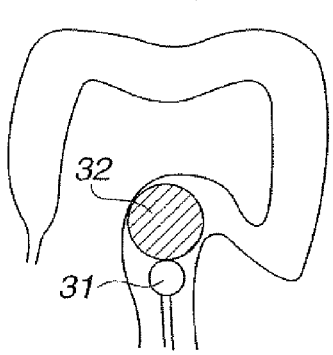
Figure 5E:
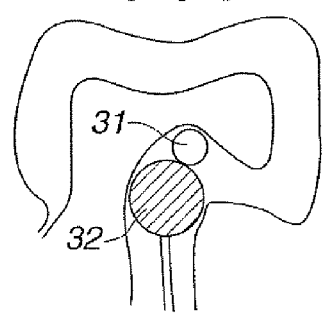
Figure 5F:
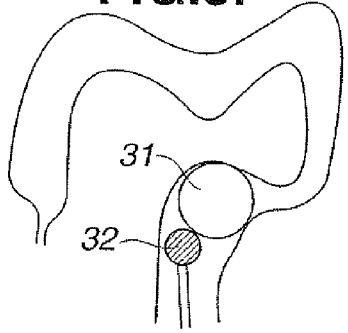
Figure 5G:
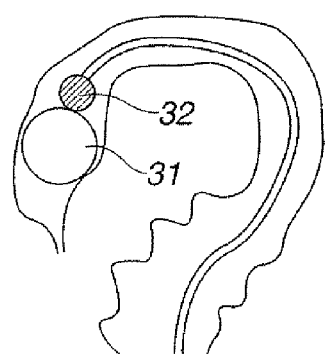
Figure 5H:
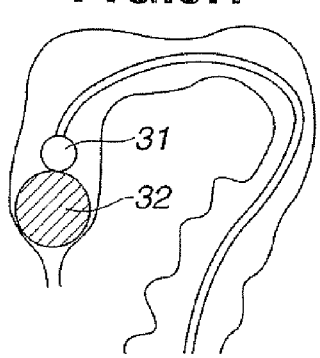

(7) FIG. 5G and FIG. 5H:

Reiterating the procedure described above, the distal end portions 21 and 22 are permitted to advance toward a deeper intestinal portion, reliably tugging the intestinal tract.

In other words, the sequentially reiterated manipulations of the apparatus for advancing an endoscope include: a manipulation for fixing the first medical instrument 2a to the intestinal wall 9; a manipulation for advancing the distal end portion 22 of the second medical instrument 2b to reach a portion located deeper than the fixing spot of the first medical instrument 2a; a manipulation for fixing the second medical instrument 2b to the intestinal wall 9; a manipulation for releasing fixation between the first medical instrument 2a and the intestinal wall; and a manipulation for advancing the distal end portion 21 of the first medical instrument 2a to reach a portion located deeper than the fixing spot of the second medical instrument 2b.

Either of the balloon portions 31 and 32 is fixed to the intestinal wall 9 in a deeper portion, by allowing each of the plurality of distal end portions 21 and 22 having the balloon portions 31 and 32, respectively, as the fixing portions for the intestinal wall 9, to mutually pass the other. As a result, the distal end portions 21 and 22 can reliably advance toward a deeper portion. Specifically, owing to the balloon portions 31 and 32 for achieving fixation to the intestinal wall 9, while either one of the fixed distal end portions 21 and 22 is pulled to tug the intestinal tract, the other of the distal end portions 21 and 22 can be brought to a deep portion.

If an adhesion is formed in the intestinal tract of the patient, while the adhered spot is fixed by one fixing portion, i.e. the balloon portion 31 or 32, the other distal end portion 21 or 22 can be advanced. Thus, the patient does not have to suffer pain which would be caused by forcibly pulling the adhered intestinal tract.

In order to perform the above manipulations, each of the two medical instruments is required to mutually pass the other in the intestine. As described above, the conventional double-balloon type structure may allow the insertion portion to pass the portion which is fixed by the over tube having balloon. However, in the state where the balloon provided at the insertion portion is inflated to be fixed to the intestinal tract, the over tube cannot advance toward a deeper portion, passing the spot fixed by the insertion portion. In this point, the conventional double-balloon type structure is completely different from the present embodiment.

Specifically, at the time of being fixed to the intestinal wall 9, the fixing portion of the apparatus for advancing an endoscope according to the present embodiment has a cross section which is partially constricted, or in other words, notched, rather than simply circled or ringed, for example. As a result, a space is formed between the fixing portion and the intestinal wall 9, which can serve as a passing zone for the medical instruments. That is, a space is formed over the spot fixed by the fixing portion, through which a deeper portion of the intestinal tract can be seen. Thus, the other non-fixed medical instrument can move through the space toward a deep intestinal portion.

As described above, a space, or a notch, can be ensured between the intestinal wall 9 and each of the medical instruments, so that the spot fixed by one medical instrument can be passed by the other medical instrument for advancement to a deeper portion. During this course of movement, each of the medical instruments can advance without hindering the movement of the other.

There may be a case where no notch is formed in the cross section of the gap between the balloon portion 31 as a fixing portion of the medical instrument 2a and the intestinal wall 9, such as the case of a doughnut shape, when the balloon portion 31 is in a fixing state. In such a case, it is true that the medical instrument 2b can advance toward a deep intestinal portion, passing the center of the doughnut shape. However, the subsequent manipulation of shrinking the balloon portion 31 of the medical instrument 2a for release from the fixation, may not allow the medical instrument 2b to pass the medical instrument 2a for further advancement toward a deeper intestinal portion. That is to say, the object of the present embodiment cannot be achieved in this case.

The endoscope apparatus 1 of the present embodiment is provided with the first medical instrument 2a and the second medical instrument 2b. Each of the medical instruments 2a and 2b is provided therein with endoscopic functions, including functions of image pick-up means, illuminating means for illuminating an observed region, air supplying means, water/air supplying means and sucking means. Also, the distal end portions 21 and 22 of the medical instruments may have a bending mechanism for controlling the direction of the distal ends.

The number of the medical instruments is not limited to two, but may be three or more. No problem may arise even if one or more medical instruments, excluding one having endoscopic functions, may not substantially have the endoscopic functions, that is, may have only a function of aiding advancement. Namely, it would be satisfactory if at least one medical instrument has the various functions, such as the image pick-up function, which should originally be exerted by an endoscope. Other medical instruments may be usable as medical instruments of the present embodiment if only each of them has a fixing portion, for example, for contributing to the advancement. Other medical instruments without having the endoscopic functions may be used when the medical instrument having the endoscopic functions is advanced toward the deep intestinal portion. Use of such an apparatus without having the endoscopic functions for advancing an endoscope provided with medical instruments, can reduce the number of members to be accommodated in each of the medical instruments, whereby the diameter of each medical instrument can be reduced. Alternatively, the functions which are usually possessed by a single endoscope may be distributed to a plurality of medical instruments. For example, a configuration may be provided, which includes a medical instrument only having a function of supplying water. Water can be supplied to the outer tube walls of other medical instruments from this medical instrument only having the function of supplying water, whereby good sliding properties can be attained for the intestinal wall and thus advancement can be facilitated.

The apparatus for advancing an endoscope according to the present embodiment has the sheath 40 bundling the medical instruments 2a and 2b. The sheath 40, which covers and bundles substantially the entire length of the two medical instruments 2a and 2b, can retain a relative positional relationship which allows each of the two medical instruments to pass the other in the intestinal tract. In other words, the sheath 40 can retain a certain inter-axis distance between the two medical instruments. Such a retaining portion for retaining an inter-axis distance between the medical instruments may not be limited to the sheath 40, but various structures may be used including the modifications provided below.

As described above, the apparatus for advancing an endoscope according to the present embodiment includes a plurality of medical instruments, at least one of which has endoscopic functions, wherein: each of the medical instruments has a distal end portion which is provided with a fixing portion enabling fixation to an intestinal wall; and the plurality of fixing portions provided at the plurality of medical instruments are configured to mutually form a gap so that when at least one of the plurality of fixing portions presses the intestinal wall, one or more other distal end portions having the fixing portions than at least the one of the plurality of fixing portions can be advanced through the gap.

The apparatus for advancing an endoscope according to the present embodiment is able to advance an endoscope into a deep intestinal portion with simple manipulations.

Figure 6A:
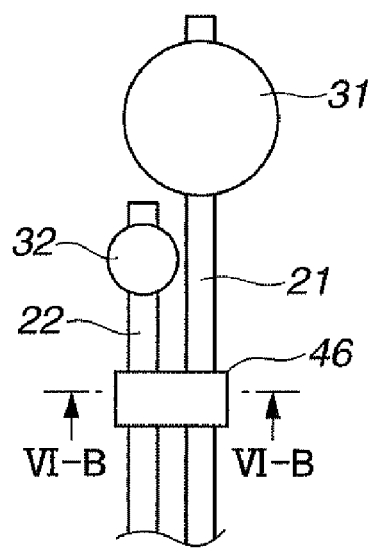
FIGS. 6A and 6B are explanatory views each illustrating a mating clip according to a first modification of the first embodiment.
Figure 6B:
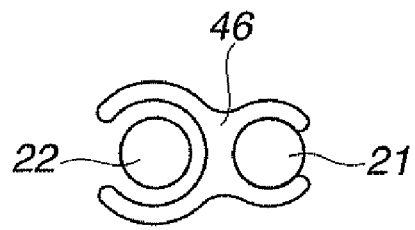

FIGS. 6A and 6B are explanatory views illustrating a mating clip serving as a retaining portion for retaining the inter-axis distance between medical instruments used for a first modification of the apparatus for advancing an endoscope according to the present embodiment. Specifically, as shown in FIGS. 6A and 6B, the first modification uses a mating clip 46 for mating the medical instruments 2a and the medical instruments 2b, instead of the sheath 40. FIG. 6A illustrates an outline of the medical instruments 2a and 2b mated by the mating clip 46. FIG. 6B is a cross-sectional view of the medical instruments 2a and 2b mated by the mating clip 46, taken along a line VI-B-VI-B of FIG. 6A. The distal end portion 21 of the medical instrument 2a and the clip 46 are firmly fixed, while the distal end portion 22 of the medical instrument 2b and the clip 46 are loosely fixed because of the necessity of relative movement along the axial direction.

Figure 7A:
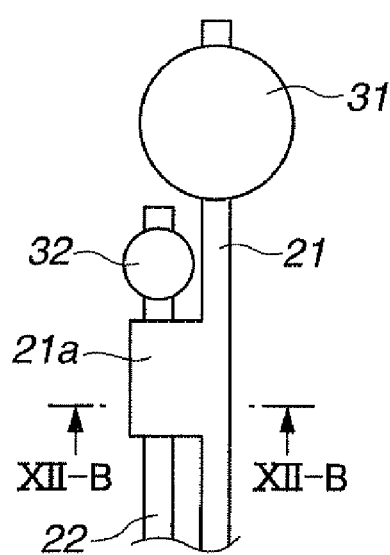
Figure 7B:
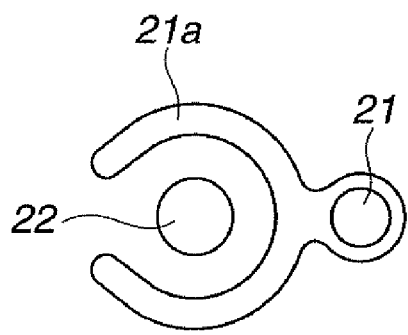

FIG. 7A is a top view illustrating the distal end portions of the apparatus 3 for advancing an endoscope having a mating projection 21a which serves as a retaining portion for retaining the inter-axis distance between medical instruments used in a second modification of the apparatus for advancing an endoscope according to the present embodiment. FIG. 7B is a cross-sectional view taken along a line XII-B-XII-B of FIG. 7A. Specifically, the distal end portion 21 may have the mating projection 21a in a predetermined region proximate to an end thereof, for loose coupling with the distal end portion 22 of the medical instrument 2b.

It should be appreciated that the sheath 40, the mating clip 46 or the mating projection 21a (hereinafter referred to as "sheath or the like") serving as a retaining portion for retaining the inter-axis distance between the medical instruments is not an essential component of the apparatus for advancing an endoscope according to the present embodiment. The sheath or the like is just a member for retaining the relative positional relationship, i.e. the inter-axis distance, between the plurality of medical instruments, for mutually enabling each of the medical instruments to pass the others in the intestinal tract. The apparatus for advancing an endoscope having such a retaining portion may facilitate each of the medical instruments mutually passing the others in an intestine. However, in the case of an endoscope in which each of all the medical instruments is provided with the image pick-up means, for example, the distal end portion of each medical instrument can be advanced, while having its image pick-up means observe the spaces between the balloons located in a deeper portion and the intestinal wall. In such a case, no sheath or the like may be required.

Also, in the case where the medical instrument fixed by the balloons has an image pick-up portion and a bending portion enabling 180-bending, the distal end portion may be bent by 180° with the bending portion. Thus, while the space between the fixed balloons and the intestinal wall 9 is observed by the image pick-up portion of the fixed distal end portion, the distal end portion of the subsequent medical instrument may be permitted to be advanced. In such a case, no sheath or the like may be required.

The two medical instruments 2a and 2b can be independently manipulated, and thus are respectively provided, for example, with: the balloon portions 31 and 32 to serve as fixing portions 30 for achieving fixation to the intestinal wall 9; the operation portions 51 and 52 for manipulating the medical instruments 2a and 2b; and connecting cords 61 and 62 for connecting the medical instruments 2a and 2b to the processor 102.

In each medical instrument, the fixing balloon portions 31 and 32 are fixed by a portion such as adhesion, for example, to the bending portion of the distal end portion of each of the medical instruments, to the distal end portion located nearer to the side of the proximal end than to the bending portion, or to a spot bridging the both. The positions of the balloon portions are not necessarily located at the distal ends of the medical instruments, but may only be located near the distal ends.

Figure 8:
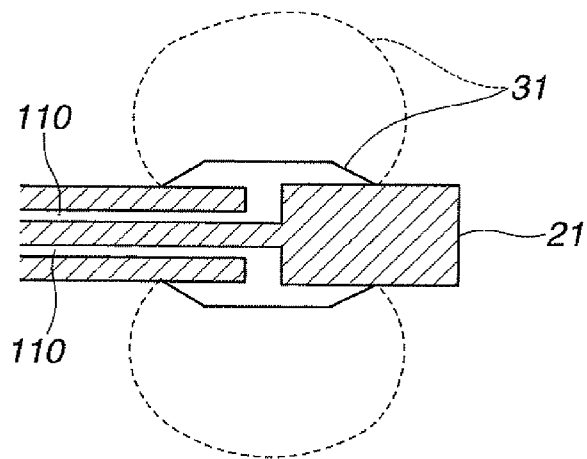
FIG. 8 is an explanatory view illustrating a balloon portion for fixation according to the first embodiment.

FIG. 8 is an explanatory view illustrating a configuration of the balloon portion, or a fixing portion, according to the present embodiment. As shown in FIG. 8, the fixing balloon portion 31 is provided with an air-supply/deairing tube 110 for taking in and out air to/from the two balloons attached to the distal end portion 21. In FIG. 8, the solid line and the broken line indicate the states of the balloon portion 31 before supplying air and after supplying air, respectively. The air-supply/deairing tube 110 may be disposed along the outer surface of the distal end portion 21. As to the other distal end portion 22 as well, an air-supply/deairing tube is connected to the balloon portion 32 in the similar manner. In FIG. 8, all the members having no direct relationship with the balloons are omitted.

Figure 9:
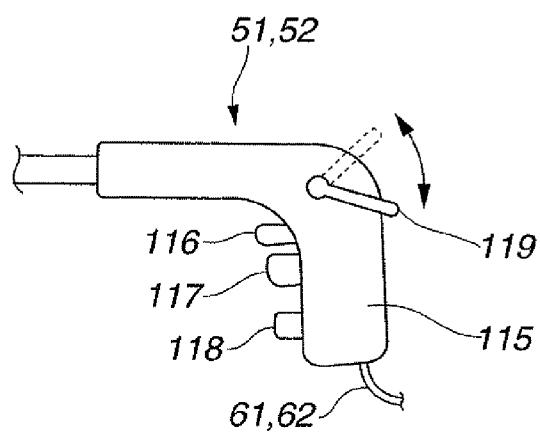
FIG. 9 is an explanatory view illustrating an operation portion according to the first embodiment.

FIG. 9 shows the operation portion 51 or 52 of the present embodiment. The operation portion 51 or 52 is provided with a grasping portion 115, an air-supply/deairing button 116, an air/water supply button 117, a suction button 118 and an angle lever 119. The grasping portion 115 can be grasped with one hand by an operator and the buttons mentioned above can be operated with one hand by the operator. In the present embodiment, in consideration of reducing fatigue of the operator, the grasping portion 115 can be grasped at a certain angle, in particular, but not limited to, at right angle, to the axis of the medical instrument 2a or 2b. The button 116, 117 or 118 is provided, when the grasping portion 115 is being grasped, within a range that enables operation of these buttons with a finger other than a thumb. The angle lever 119 can be operated with a first finger.

Figure 10:
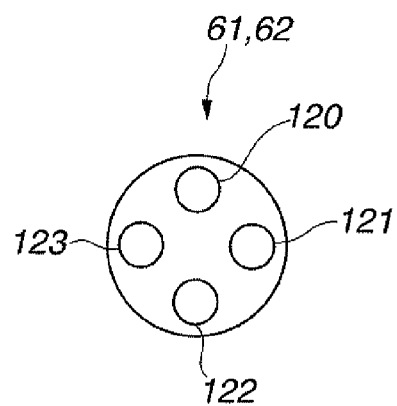
FIG. 10 is a cross-sectional view illustrating cords according to the first embodiment.

FIG. 10 shows a cross section of the cord 61 or 62 connecting the medical instrument 2a or 2b to the processor 102. The cord 61 or 62 is inserted with an air-supply/deairing tube 120 for operating the balloon portion 31 or 32, an air/water supply tube 121, a suction tube 122 and a cable 123 for operating the image pick-up portion and a light source. The cord 61 or 62 connected to the operation portion 51 or 52 is led out from a position that would not cause interruption to the operator. The cord 61 or 62 may be branched midway, so that the air-supply/deairing tube 120, the air/water supply tube 121 and the suction tube 122 can be connected to the pump 103, and the cable 123 can be connected to the processor 102.

The balloon portions 31 and 32 are made, for example, of silicone rubber having excellent elasticity. Alternatively, depending on the structure, the balloon portions 31 and 32 may be made of a material, such as resin or paper, which per se has small elasticity.

In order to enhance slidability for the intestine, an outer surface of each medical instrument may be coated with a lubricant or a coating material.

In each of the medical instruments 2a and 2b are incorporated for example, a tube 111 for supplying air, a tube 112 for supplying water, a tube 113 for performing suction and a cable 114 for transmitting image pick-up signals and power source for illumination. The tubes 111, 112 and 113 as well as the cable 114, for example, are detachably connected to the processor 102 or the pump 103. In the case where each of the medical instruments 2a and 2b has a bending function, i.e. has a bending portion, a wire or a tube, for example, for causing a bending movement is additionally incorporated in each of the medical instruments 2a and 2b.

The medical instruments 2a and 2b are rubbed with each other in the sheath 40 and the intestinal wall 9. In order to reduce the advancing force without deteriorating the mutual advancing properties of the distal end portions 21 and 22, the surfaces of the medical instruments 2a and 2% as well as the inner and outer surfaces of the sheath 40 are coated with a material having high slidability. For example, the sheath 40 may be made of a fluorine resin having high slidability. Also, the inner surface of the sheath 40 may be made lubricious by applying a lubricant or a special coating. The sheath 40 may preferably have excellent bending properties.

The sheath 40 is fixed to either of the medical instruments 2a and 2b. The end portions of the sheath 40 are processed so as to be rounded or tapered lest the intestinal wall is damaged by the end portions. The flexible tube portions of the medical instruments 2a and 2b are each structured so that the flexible tube portion on the side of the proximal end portion is more rigid than the flexible tube portion in the distal end portion to prevent the flexible tube portion from being easily bent. Thus, the flexible tube portions may provide enhanced operability for advancement and durability against repeated pushing and pulling.

In the case where there are a plurality of medical instruments each having an image pick-up portion, a selecting portion may be provided, through which the operator can select an image to be displayed on the monitor 101. Alternatively, in this case, a plurality of images may be simultaneously displayed, or a plurality of monitors may be provided. Further, in order to observe the space between the distal end portion of the fixed medical instrument and the intestinal wall during advancement operation, a displaying section may be such that the image pick-up portions used for display are automatically switched, so that the images picked up by the image pick-up portion of the medical instrument advancing through the space can be displayed.

Referring now to FIGS. 11A to 17C, hereinafter are explained fixing portions according to various modifications of the first embodiment of the present invention. It should be appreciated that these figures are schematic views, and thus those members and specific thicknesses or the like of the balloon walls are omitted, which are not directly related to the explanation.

Figure 11A:
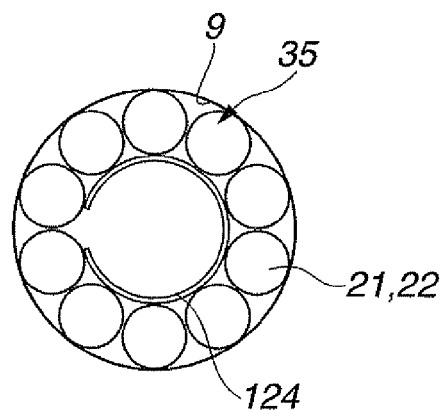
FIG. 11A is a cross-sectional view illustrating a fixing portion in a state where the balloon portion is inflated according to a second modification of the first embodiment.
Figure 11B:
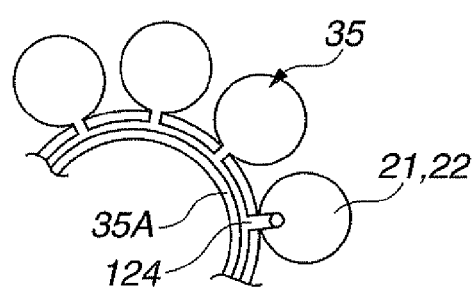
FIG. 11B is a partially enlarged view of FIG. 11A.
Figure 12A:
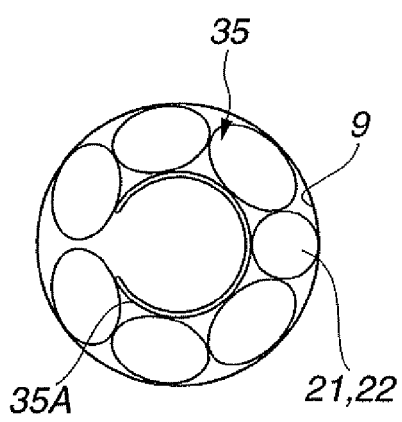
FIGS. 12A to 12C are views each illustrating a fixing portion according to a third modification of the first embodiment.
Figure 12B:
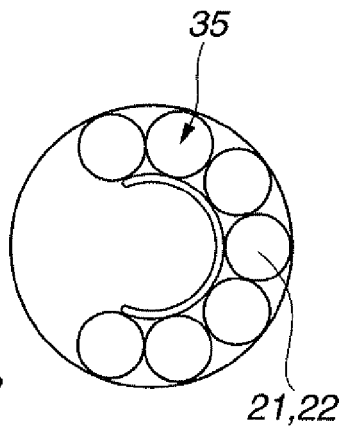
Figure 12C:
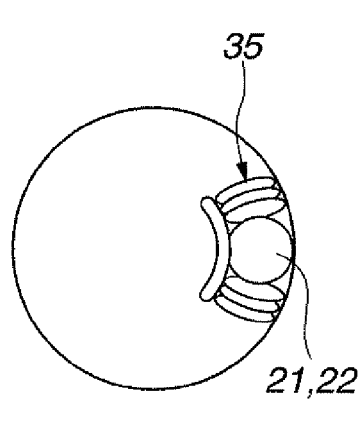
Figure 13A:
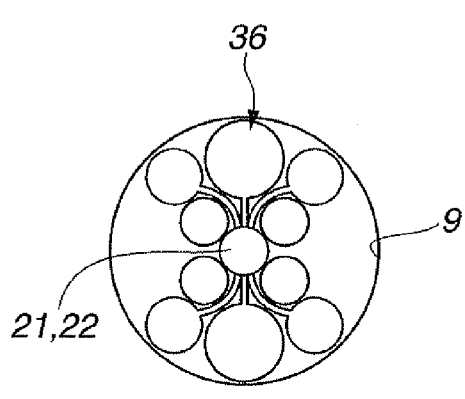
FIG. 13A is a cross-sectional view illustrating a fixing portion in a state where the balloon portion is inflated according to a fourth modification of the first embodiment.
Figure 13B:
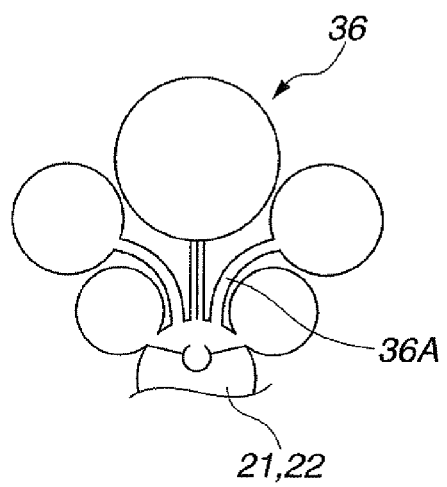
FIG. 13B is a partially enlarged view of FIG. 13A.

FIGS. 11A and 11B illustrate a fixing portion according to a second modification of the first embodiment. FIG. 11A is a schematic cross-sectional view of the fixing portion in a state of being inflated. FIG. 11B is a partially enlarged view (the intestinal wall 9 is not shown) of FIG. 11A. FIGS. 12A to 12C illustrate a fixing portion according to a third modification of the first embodiment. These figures show changes in the fixing portion from a state where the balloon portion is inflated as illustrated in FIG. 12A to a state where the balloon portion is shrunk as illustrated in FIG. 12C. FIGS. 13A and 13B illustrate a fixing portion according to a fourth modification of the first embodiment of the present invention. FIG. 13B is a partially enlarged view (the intestinal wall 9 is not shown) of FIG. 13A.

Figure 14A:
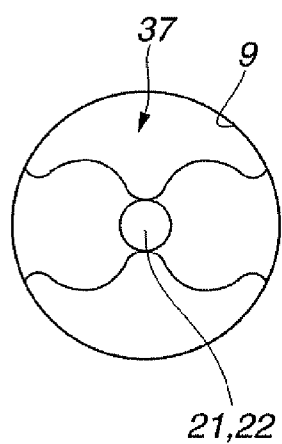
FIGS. 14A to 14C are cross-sectional views each illustrating an example of a change in the region occupied by the fixing portion in an intestine, when the fixing portion is inflated/shrunk according to a fifth modification of the first embodiment.
Figure 14B:
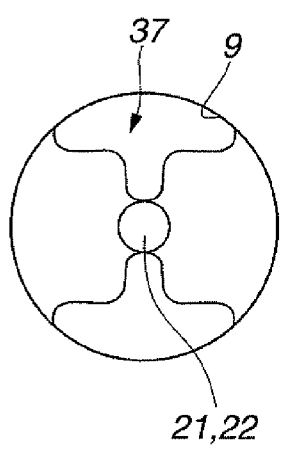
Figure 14C:
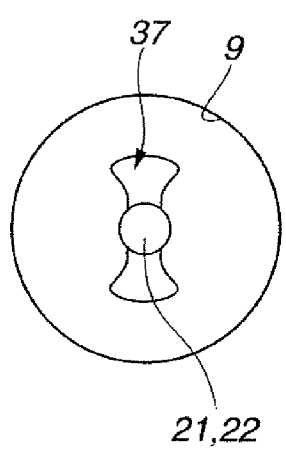
Figure 15:
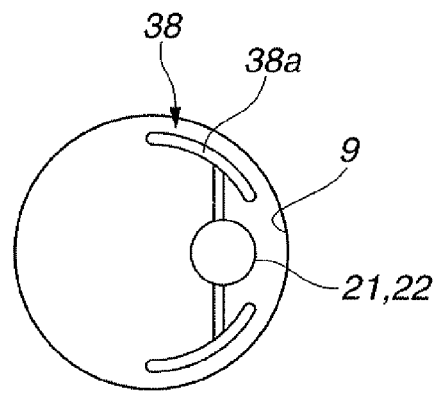
FIG. 15 is a schematic view illustrating a fixing portion as viewed from an axial direction of the distal end portion according to a sixth modification of the first embodiment.
Figure 16A:
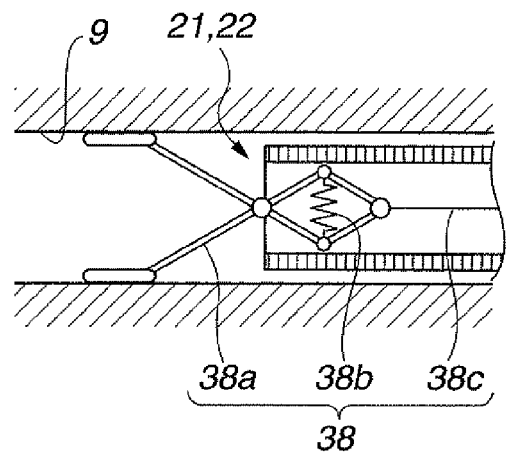
FIG. 16A is a cross-sectional view illustrating the fixing portion in a fixed state as viewed from a direction perpendicular to the longitudinal direction of the distal end portion according to the sixth modification of the first embodiment.
Figure 16B:
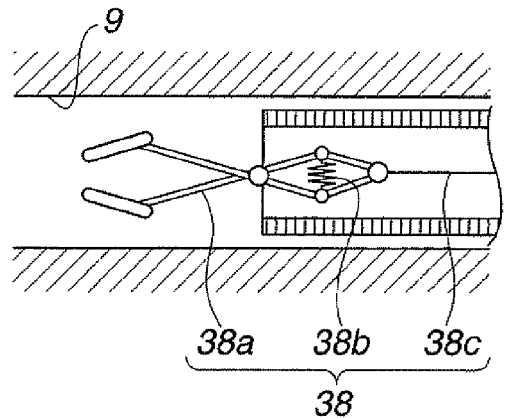
FIG. 16B is a cross-sectional view illustrating the fixing portion in a non-fixed state as viewed from a direction perpendicular to the longitudinal direction of the distal end portion according to the sixth modification of the first embodiment.
Figure 17A:
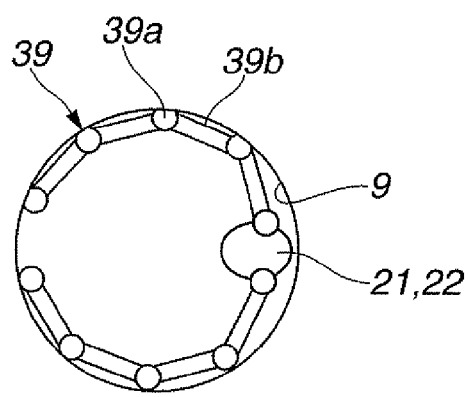
FIG. 17A is a cross-sectional view illustrating a foldable fixing portion in an unfolded state according to a seventh modification of the first embodiment.
Figure 17B:
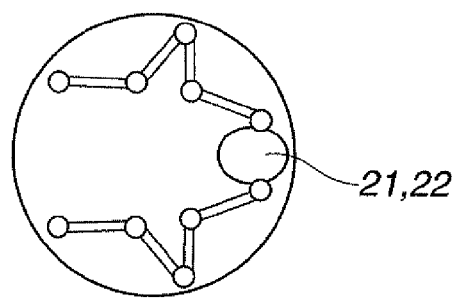
FIG. 17B is a cross-sectional view illustrating the foldable fixing portion in a state of being folded according to the seventh modification of the first embodiment.
Figure 17C:
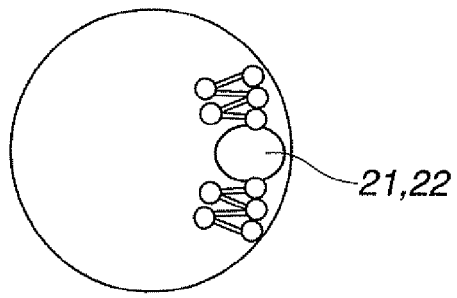
FIG. 17C is a cross-sectional view illustrating the foldable fixing portion in a folded state according to the seventh modification of the first embodiment.

FIGS. 14A to 14C are cross-sectional views illustrating an example of changes in the region occupied by a balloon portion 37, i.e. a fixing portion, according to a fifth modification of the first embodiment of the present invention. FIG. 15 is a schematic view of a fixing portion 38 according to a sixth modification of the first embodiment of the present invention, as viewed from an axial direction of the distal end portion. FIGS. 16A and 16B are cross-sectional views of the fixing portion 38 according to the sixth modification of the first embodiment of the present invention, as viewed from a direction perpendicular to the longitudinal direction of the distal end portion. FIG. 16A illustrates a fixed state and FIG. 16B illustrates a non-fixed state. FIGS. 17A to 17C illustrate a foldable fixing portion 39 according to a seventh modification of the first embodiment of the present invention. FIG. 17A illustrates an unfolded state, FIG. 17B, a state of being shrunk, and FIG. 17C, a shrunk state.

The fixing portion 30 according to the second modification of the first embodiment of the present invention, is a balloon portion 35 having a structure including a group of a plurality of balloons, as shown in FIG. 11A, the cross-sectional view of the inflated state. The plurality of balloons are fixed by an elastic connecting band 35A which is fixed to the distal end portion 21 or 22. Air is charged/discharged to/from each of the balloons through an air-supply/deairing tube 124 incorporated in the connecting band 35A. The air-supply/deairing tube 124 may be disposed at a gap of the connecting band.

As shown in FIGS. 12A to 12C, in the intestinal tube cavity, the connecting band 35A is positioned inside the balloon portion 35 in the inflated state of the balloon portion 35. Thus, when the balloon portion 35 is inflated, the group of balloons substantially takes the form of a doughnut shape. When the balloon portion 35 is shrunk to release the fixation, the group of balloons takes the form of a C-shape in cross section as shown in FIG. 12B.

As shown in FIGS. 13A and 13B, the fixing portion according to the fourth modification of the first embodiment of the present invention, is a balloon portion 36 having a structure including a number of balloons. As shown in FIG. 13B, the balloons are indirectly fixed to the distal end portion 21 or 22 through an air-supply/deairing tube 36A. With the configuration explained above, when the balloons are inflated, the shape of the balloon portion 36 occupying the spot of fixation can be changed.

FIGS. 14A to 14C illustrate an example of changes in the region occupied by the balloon portion 37, i.e. a fixing portion, according to the fifth modification of the first embodiment of the present invention, FIG. 14A illustrates a state where the balloon portion 37 is inflated and FIG. 14C, a state where the balloon portion 37 is shrunk. FIG. 14B illustrates an intermediate state of the balloon portion 37 between inflated and shrunk states. As shown in FIG. 14A, the balloon portion 37 is inflated in a flattened shape unlike the ordinary balloons.

FIG. 15 illustrates the fixing portion 38 according to the sixth modification of the first embodiment of the present invention, as viewed from an axial direction of the distal end portion. FIGS. 16A and 16B are cross-sectional views of the fixing portion 38 according to the sixth modification of the first embodiment of the present invention, as viewed from a direction perpendicular to the longitudinal direction of the distal end portion. FIG. 16A illustrates a fixed state and FIG. 16B illustrates a non-fixed state. FIGS. 16A and 16B are explanatory views explaining the operation. In order to indicate the interior of the distal end portion 21 or 22, the diameter of the distal end portion 21 or 22 is indicated on a grand scale.

The fixing portion 38 is an extensible mechanical member. In particular, the fixing portion 38 includes a plurality of fixing arms 38a and provided with an arm strut spring 38b. As shown in FIG. 16A, an arm manipulating wire 38c is connected to a proximal end portion of the arms, passing through the interior of the distal end portion 21 or 22 and extending to the operation portion. When the spring 38b is in a non-loaded state, the arms 38a are open, or extended, so that the fixing portion 38 can be fixed to the intestinal wall 9. As shown in FIG. 16B, when the wire 38c is pulled, the arms 38a are folded, or shrunk, so that the fixation between the fixing portion 38 and the intestinal wall 9 can be released.

FIGS. 17A to 17C illustrate the foldable fixing portion 39 according to the seventh modification of the first embodiment of the present invention. FIG. 17A illustrates an unfolded state, FIG. 17B, a state of being shrunk, and FIG. 17C, a shrunk state. The fixing portion 39 is an extensible mechanical member and has a structure in which a plurality of members 39b are linked through joints 39a in a foldable manner.

The fixing portion 39, when fixed, is in the state as shown in FIG. 17A, and when released, is in the sate as shown in FIG. 17C through the state of FIG. 17B, so as to be small enough for accommodation.

No problem will be raised if the apparatus for advancing an endoscope of the present embodiment has a plurality of medical instruments whose fixing portions individually have different systems, shapes or sizes.

In the first embodiment of the present invention, the description has been given on the apparatus 3 for advancing an endoscope, having two medical instruments 2a and 2b for simplification of the explanation. However, the apparatus for advancing an endoscope may have three or more medical instruments. Hereinafter is described the apparatus for advancing an endoscope having a plurality of medical instruments.

The apparatus for advancing an endoscope having a plurality of medical instruments refers to one in which at least one medical instrument has the endoscopic functions, and each of the plurality of medical instruments has at its distal end a fixing portion which can be fixed to the intestinal wall. In such an apparatus for advancing an endoscope, the following manipulations are reiterated in the following order, that is: a manipulation of fixing one selected medical instrument to the intestinal wall 9; a manipulation of advancing the distal end portion of a medical instrument which is not fixed to the intestinal wall 9 toward a portion located deeper than the fixing spot of the fixed medical instrument and the intestinal wall 9; and a manipulation of fixing the advanced medical instrument to the intestinal wall 9 at the deeper portion. Through these manipulations, all the medical instruments are fixed to the intestinal wall 9. After that, the following manipulations are performed, which are: a manipulation of releasing the medical instrument from fixation to the intestinal wall 9, which has been fixed to the intestinal wall 9 in a shallowest portion, i.e. the medical instrument that has been firstly subjected to the fixing manipulation; a manipulation of advancing the distal end portion of the medical instrument that has been released from fixation toward a portion located deeper than the fixing spots of any of the already fixed medical instruments; and a manipulation of fixing the medical instrument released from fixation to the intestinal wall 9. Further, these manipulations are followed by: a manipulation of releasing the medical instrument from fixation to the intestinal wall 9, which has turned out to be fixed to the intestinal wall 9 in a shallowest portion as a result of the foregoing manipulations; a manipulation of advancing the distal end portion of the medical instrument released from fixation to a portion located deeper than the fixing spots of any of the already fixed medical instruments; and a manipulation of fixing the medical instrument released from fixation to the intestinal wall 9. Reiteration of these manipulations can advance the insertion portions to a deep portion. As a matter of course, these manipulations for advancement are completed at the point when the medical instrument having the endoscopic functions has reached a desired deep portion.

Second Embodiment

Hereinafter is described an apparatus 3A for advancing an endoscope, according to a second embodiment of the present invention.

Figure 18:
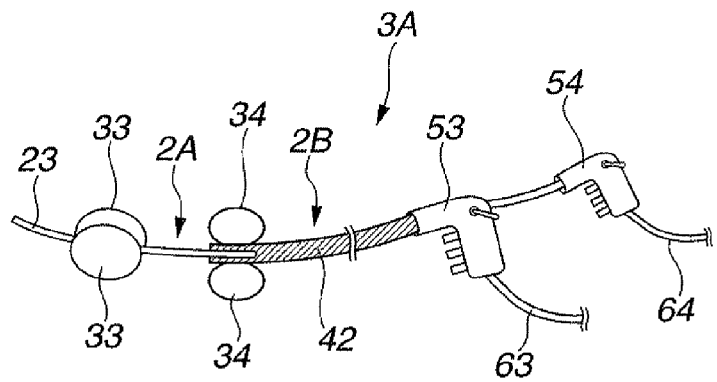
FIG. 18 is an outline view of an apparatus for advancing an endoscope according to a second embodiment of the present invention.

FIG. 18 is an outline view of the apparatus 3A for advancing an endoscope. The general configuration of the apparatus 3A for advancing an endoscope is substantially the same as that of the first embodiment, except that the apparatus 3A for advancing an endoscope includes a medical instrument 2A having at the end thereof a distal end portion 23, and an over tube 42 having at the end thereof a notched portion 42a. The medical instrument 2A and the over tube 42 have fixing portions 33 and 34, respectively, which can be independently manipulated.

The apparatus for advancing an endoscope according to the present embodiment has two medical instruments, in which a first medical instrument has the endoscopic functions and a second medical instrument has no endoscopic functions. Specifically, the medical instrument 2A having the distal end portion 23 corresponds to the first medical instrument, and a medical instrument 2B having the over tube 42 corresponds to the second medical instrument.

Figure 19:
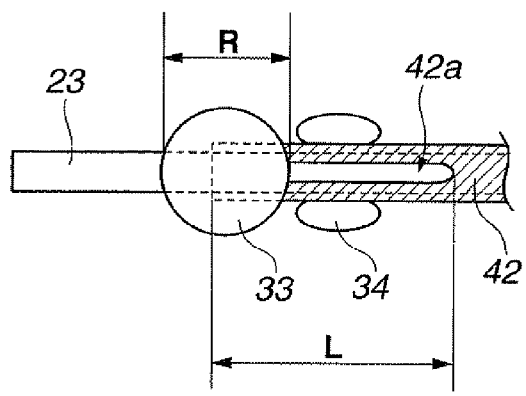
FIG. 19 is a cross-sectional view of a distal end portion of the apparatus for advancing an endoscope according to the second embodiment.

FIG. 19 is a cross-sectional view of a distal end portion of the apparatus 3A for advancing an endoscope according to the second embodiment. In particular, FIG. 19 shows a state where a balloon portion 33 serving as a fixing portion of the first medical instrument 2A is inflated, and the first medical instrument 2A having the endoscopic functions is fixed to the intestinal wall (not shown).

Figure 20:
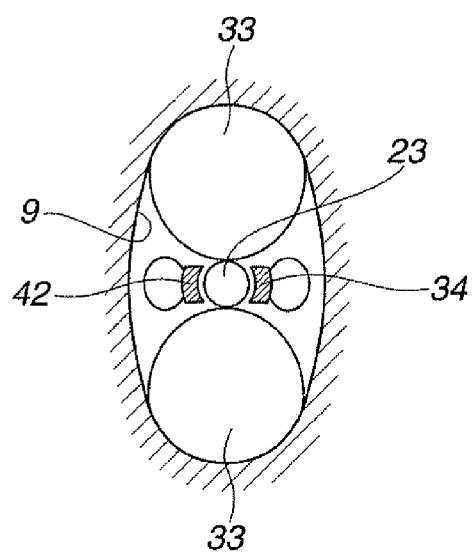
FIG. 20 is a view illustrating the apparatus for advancing an endoscope as viewed from the side of a deep intestinal portion according to the second embodiment.

FIG. 20 illustrates the distal end portion of the apparatus 3A for advancing an endoscope as viewed from the side of a deep intestinal portion. In FIG. 20, similar to FIG. 19, the balloon portion 33 is inflated, and the first medical instrument 2A is fixed to the intestinal wall 9. In this state, the balloon portion 33 is positioned in a deep intestinal portion located deeper than the balloon portion 34 for fixing the over tube 42. Also, the balloon portion 34 for fixing the over tube is in a shrunk state, and thus the over tube is not fixed to the intestinal wall 9.

As is apparent from FIG. 20, in the state where the balloon portion 33 is inflated for fixation to the intestinal wall 9, a space is ensured between the balloon portion 33 and the intestinal wall 9, which is sufficient for advancing the distal end portion of the over tube 42 having the shrunk balloon portion 34. Thus, in this state, the distal end portion of the over tube 42 having the balloon portion 34 can advance toward a portion located deeper than the balloon portion 33.

Figure 21:
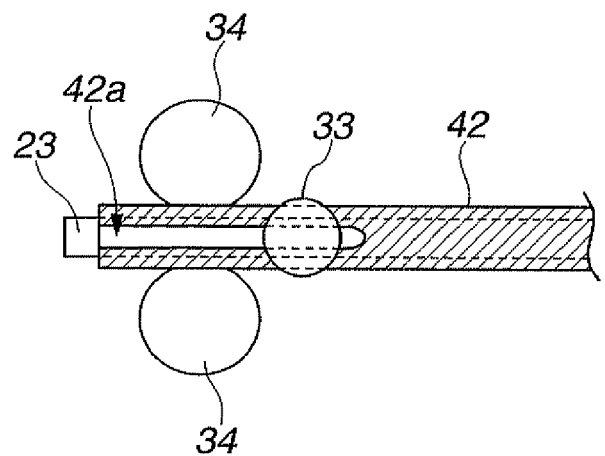
FIG. 21 is a cross-sectional view of a distal end portion of an apparatus 3A for advancing an endoscope according to the second embodiment.

FIG. 21 is a cross-sectional view of the distal end portion of the apparatus 3A for advancing an endoscope according to the second embodiment. As shown in FIG. 21, the balloon portion 34 for fixing the over tube 42 is inflated and fixed to the intestinal wall 9 (not shown). Then, when the balloon portion 33 for fixing the first medical instrument 2A is shrunk, the distal end portion 23 having the balloon portion 33 can then advance toward a deep portion. Specifically, the balloon portion 33 at the distal end portion 23 can again advance toward a portion located deeper than the balloon portion 34 for fixing the over tube 42. Reiteration of the above manipulations can reliably advance the medical instrument 2A having the endoscopic functions toward a deep portion.

As shown in FIG. 18, the apparatus 3A for advancing an endoscope has two-layer structure made up of the first medical instrument 2A and the over tube 42 serving as the second medical instrument 2B. The first and second medical instruments 2A and 21 are provided with operation portions 54 and 53, respectively, to perform various controls, such as advancement, removal, air supply, water supply, or suction. Further, the operation portions 53 and 54 are connected, for example, to cords 63 and 64, respectively, each incorporating, for example, an air-supply/deairing tube, an air/water supply tube and a suction tube. The first medical instrument 2A may further be provided with a bending portion which is to be controlled by the operation portion 54.

A length L of the notched portion 42a at the end of the over tube 42 may preferably be larger by a factor of two or more than a diameter R of each of the balloons for fixing the first medical instrument 2A. With the length L exceeding this range, the over tube 42, when sliding over the medical instrument 2A, will not be interfered by the balloon portion 33 for fixing the first medical instrument, so that the balloon portion 34 for fixing the over tube can advance toward a portion located deeper than the balloon portion 33 for fixing the first medical instrument.

No particular upper limit is provided for the length L of the notched portion 42a; however, considering the operability or strength, the length L may preferably be three times or less of the diameter R of each of the balloons for fixing the first medical instrument. It should be appreciated that the diameter R of the balloon portion 33 used for fixation refers, as shown in FIG. 19, to the length in the axial direction of the medical instrument in the state where the balloon is inflated and fixed in the intestine.

Figure 23:
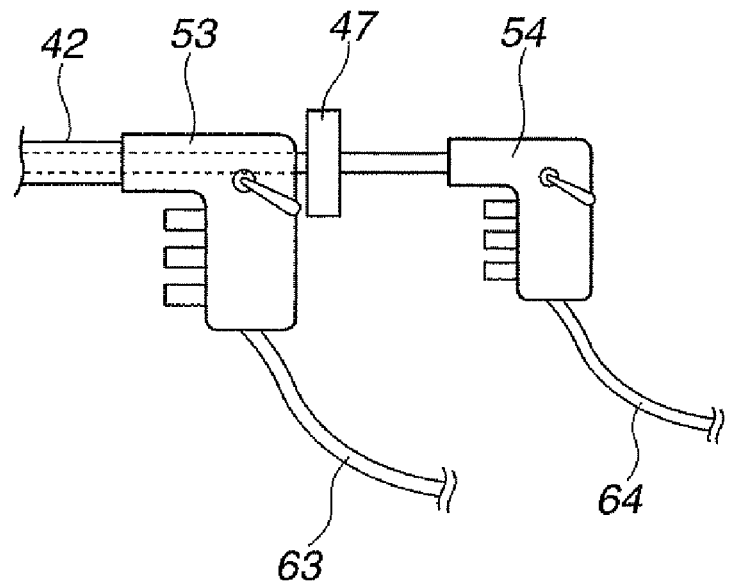
FIG. 23 is a schematic view of an operation portion of the apparatus for advancing an endoscope according to the second embodiment.

FIG. 23 is a schematic view of the operation portions of the apparatus 3A for advancing an endoscope. In the apparatus 3A for advancing an endoscope according to the second embodiment, it is required that the end of the over tube is prevented from escaping to the rear end side from the balloon portion 33 for fixing the first medical instrument, when the balloon portion 34 for fixing the over tube is located in a shallower place than the balloon portion 33 for fixing the medical instrument. This is for smoothly reiterating sliding operation of the over tube 42 and the distal end portion 23 of the medical instrument 2A. To this end, it is preferred that a stopper 47 is provided in the vicinity of the operation portion, as shown in FIG. 23, for adjusting the sliding.

Figure 22:
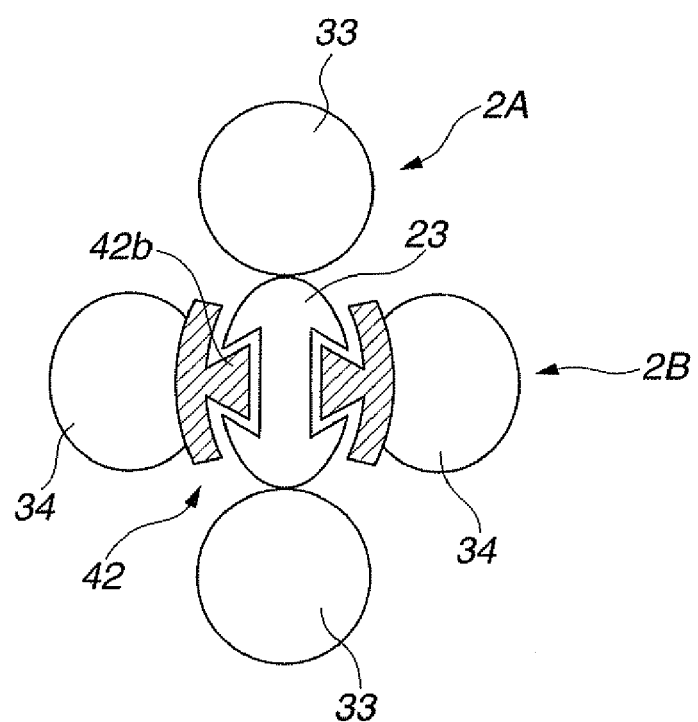
FIG. 22 is a cross-sectional view illustrating a distal end portion of the apparatus 3A for advancing an endoscope according to a first modification of the second embodiment.

FIG. 22 is a schematic view of the distal end portion 23 at the vicinity near the distal end of the apparatus 3A for advancing an endoscope according to a first modification of the second embodiment, as viewed from a direction perpendicular to the axial direction. In the first modification of the second embodiment, the over tube 42 has a fitting portion 42b which is loosely fitted to the distal end portion 23 of the first medical instrument 2A. With provision of the fitting portion 42b, the distal end portion 23 and the over tube 42 are prevented from separating from each other, whereby the sliding operation can be facilitated. In particular, the fitting portion 42b of the over tube 42 may preferably be formed within a region where the notched portion 42a is present.

Figure 24:
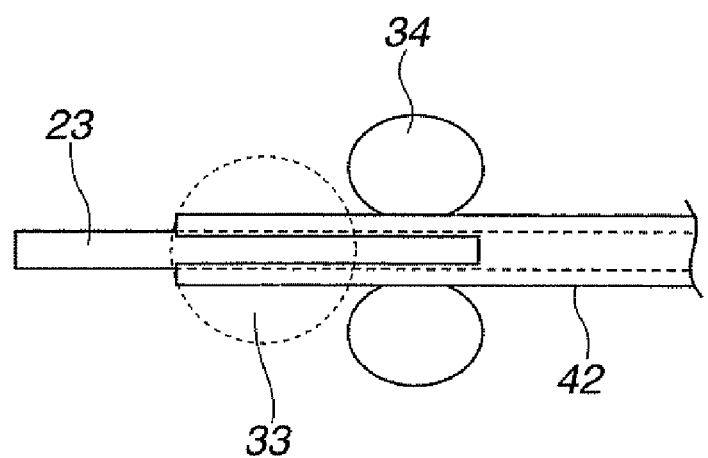
FIG. 24 is a schematic view of a distal end portion of the apparatus for advancing an endoscope according to the second embodiment.

As shown in FIG. 24, the balloon portion 34 for fixing the over tube is fixed to the over tube 42, at a proximal end side of the distal end portion of the over tube a little distanced from the end of the over tube.

A lubricant may preferably be applied in order to enhance the slidability between the over tube 42 and the distal end portion 23.

It should be appreciated that, in the manipulations for advancement, the distal end portion of the over tube 42 will not block the field of view of the image pick-up portion accommodated in the distal end portion 23 of the first medical instrument.

Third Embodiment

Hereinafter is described an apparatus for advancing an endoscope according to a third embodiment of the present invention.

Figure 25A:
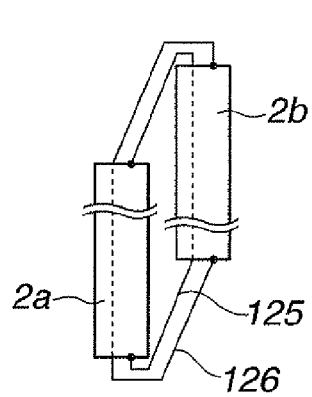
FIGS. 25A to 25C are explanatory views each illustrating a guiding mechanism using a cable according to a third embodiment of the present invention.
Figure 25B:
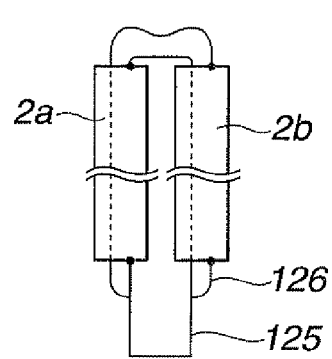
Figure 25C:
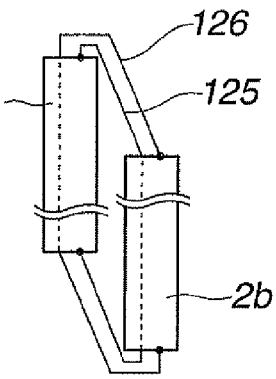

FIGS. 25A to 25C are explanatory views each illustrating a guiding mechanism using a cable, which serves as an advancement aiding member of the apparatus for advancing an endoscope for the present embodiment. Referring to FIGS. 25A to 25C, hereinafter is described the guiding mechanism using a cable, which serves as an advancement aiding member and contributes to an easier performing of the manipulations for advancement in the apparatus for advancing an endoscope according to the present embodiment. The basic configuration of the apparatus for advancing an endoscope according to the present embodiment is the same as that of the apparatus for advancing an endoscope according to the first embodiment, with an exception that the apparatus for advancing an endoscope according to the third embodiment has the guiding mechanism using a cable, as an advancement aiding member.

Specifically, as shown in FIGS. 25A to 25C, both ends of a cable 125 serving as the advancement aiding member are fixed to the forefront end and the rear end of the second medical instrument 2b, with the portion therebetween being inserted through the first medical instrument 2a. On the other hand, both ends of a cable 126 serving as the advancement aiding member are fixed to the forefront end and the rear end of the first medical instrument 2a, with the portion therebetween being inserted through the second medical instrument 2b. In other words, the advancement aiding member is made up of the cable 125 and the cable 126. It should be appreciated that, in FIGS. 25A to 25C, those members, such as the fixing portion 30 or the operation portion 50, having no direct relationship with the guiding mechanism are all omitted.

FIG. 25A shows a state where the distal end portion of the second medical instrument 2b goes ahead of the distal end portion of the first medical instrument 2a in the intestine, being fixed by the fixing portion. That is, the upper part of the figure corresponds to the deeper intestinal portion, and the lower part of the figure corresponds to the side of the anus.

When the cable 125 is pulled in this state, the distal end portion of the first medical instrument 2a is advanced toward a deeper portion, as shown in FIG. 25B, to have the end of the distal end portion of the first medical instrument 2a juxtaposed with the end of the distal end portion of the second medical instrument 2b quite easily. Thus, the apparatus for advancing an endoscope, which is provided with the guiding mechanism having the cables, can considerably facilitate the job of manipulating the distal end portion of the first medical instrument 2a for advancement to a portion located deeper than the distal end portion of the second medical instrument 2b (FIG. 25C).

In the case where the distal end portion of the first medical instrument 2a goes ahead of the distal end portion of the second medical instrument 2b in the intestine, being fixed by the fixing portion (FIG. 25C), pulling of the cable 126 may allow the distal end portion of the second medical instrument 2b to advance and be located near the distal end portion of the first medical instrument 2a.

Figure 26:
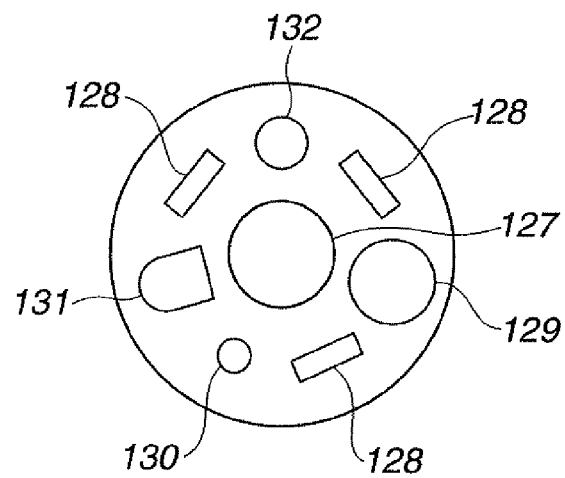
FIG. 26 is a schematic view illustrating a distal end portion of a medical instrument having the guiding mechanism cable according to the third embodiment.

FIG. 26 illustrates a configuration of an end of a medical instrument having the endoscopic functions in the apparatus for advancing an endoscope, according to the third embodiment of the present invention. The end of the endoscope includes: an image pick-up element 127 for observing the digestive tract; a plurality of illumination portions 28 for illuminating the digestive tract; a suction port 129; a front water supply port 130 for removing residue and mucus; an air/water supply base 131 for removing dirt from an image pick-up lens; and a cable insertion port 132 for inserting the cables 125 and 126 to achieve smooth operation in association with other medical instruments. The illumination portions 128 may either be made up of an optical fiber, or be made up of an electrical portion, such as an LED.

Fourth Embodiment

Figure 27:
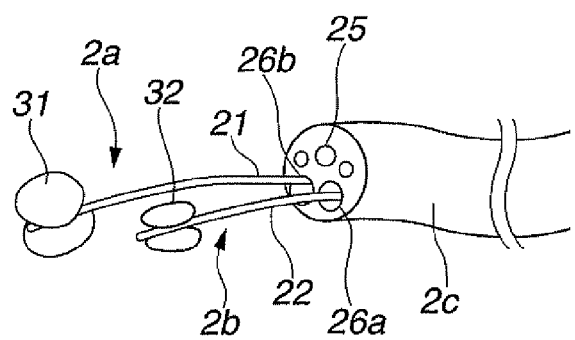
FIG. 27 is an oblique perspective view illustrating a distal end portion of an apparatus for advancing an endoscope according to a fourth embodiment of the present invention.

FIG. 27 is an oblique perspective view of a distal end portion of a medical instrument in an apparatus for advancing an endoscope, according to a fourth embodiment of the present invention. FIGS. 28A to 28G are illustrations each explaining a manipulation of the apparatus for advancing an endoscope, according to the present embodiment. The principle of basic operations of the apparatus for advancing an endoscope according to the present embodiment is the same as that of the apparatus for advancing an endoscope according to the first embodiment. As shown in FIG. 27, the apparatus for advancing an endoscope according to the present embodiment includes the medical instrument 2a having the balloon portion 31, the medical instrument 2b having the balloon portion 32, and the endoscope 2c. The endoscope 2c is provided with such an endoscopic function as picking up images performed, for example, by an image pick-up portion 25. Also, the endoscope 2c has two forceps holes 26a and 26b at its end. The medical instruments 2a and 2b can be projected through the forceps holes 26a and 26b, respectively.

Referring to FIGS. 28A to 28G, hereinafter are described the manipulations of the apparatus for advancing an endoscope according to the present embodiment. FIGS. 28A to 28G are schematic views illustrating a procedure for advancing the endoscope 2c toward a deep intestinal portion using the apparatus for advancing an endoscope according to the present embodiment, as viewed from a direction perpendicular to the longitudinal direction of the intestine.

Figure 28A:
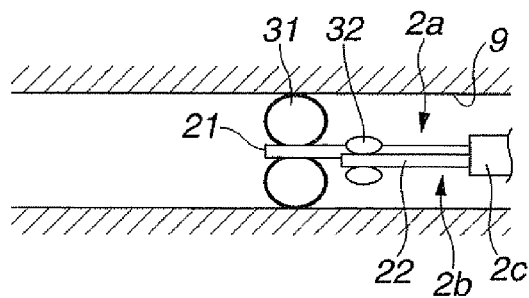
FIGS. 28A to 28G are illustrations each explaining a manipulation of the apparatus for advancing an endoscope according to the fourth embodiment.
Figure 28B:
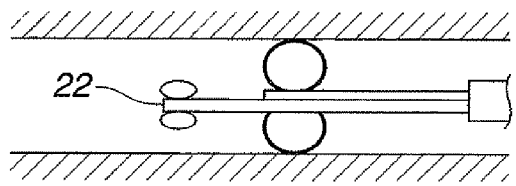
Figure 28C:
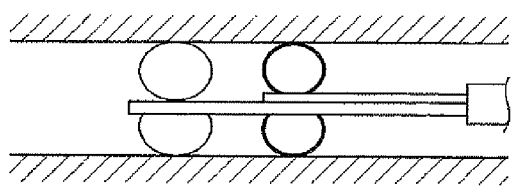
Figure 28D:
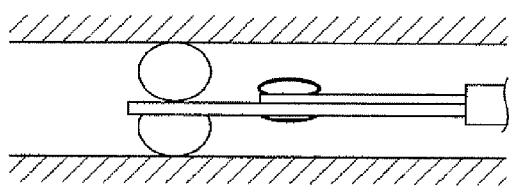
Figure 28E:
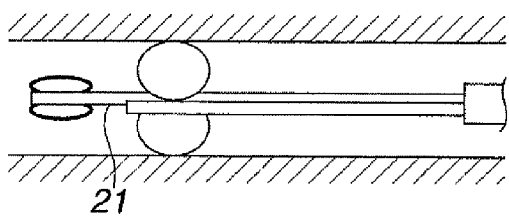
Figure 28F:
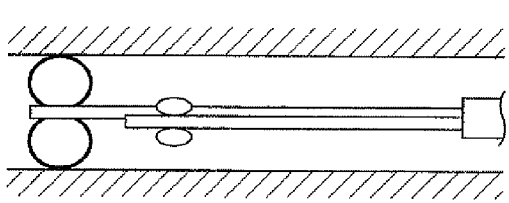

In a manipulation for advancement of the endoscope 2c performed by the apparatus for advancing an endoscope, the balloon portion 31 of the medical instrument 2a is inflated first, as shown in FIG. 28A, with the medical instrument 2a being fixed to the intestinal wall 9, while the balloon portion 32 of the medical instrument 2b is shrunk. In the apparatus for advancing an endoscope according to the present embodiment, the distal end portion 22 of the medical instrument 2b can be advanced to a deeper intestinal portion (to the left side of the figure) than the medical instrument 2a, through the gap between the medical instrument 2a and the intestinal wall 9, as shown in FIG. 28B, even when the medical instrument 2a is fixed to the intestinal wall 9. When the distal end portion 22 of the medical instrument 2b has reached a deeper intestinal portion than the distal end portion 21 of the medical instrument 2a, the balloon portion 32 of the medical instrument 2b is inflated for fixation to the intestinal wall 9 (FIG. 28C), while the balloon portion 31 of the medical instrument 2a is shrunk (FIG. 28D). Then, as shown in FIG. 28E, even in the state where the medical instrument 2b is fixed to the intestinal wall 9, the distal end portion 21 of the medical instrument 2a can now be advanced to a deeper intestinal portion (to the left side of the figure) than the medical instrument 2b, through the gap between the medical instrument 2b and the intestinal wall 9. After that, the balloon portion 31 of the medical instrument 2a is inflated again for fixation to the intestinal wall 9, as shown in FIG. 28F.

Figure 28G:
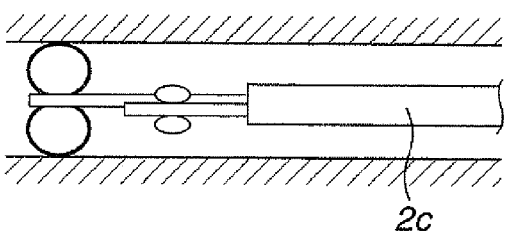
Figure 29A:
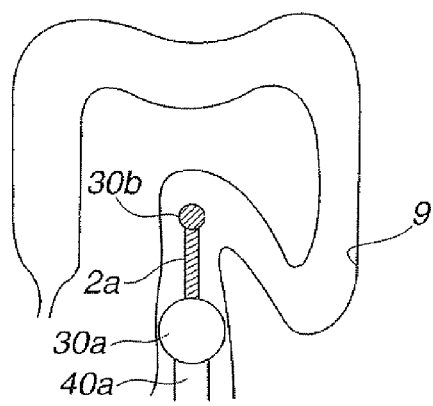
FIGS. 29A to 29H are explanatory views illustrating a procedure for advancing a conventional endoscope in a large intestine.
Figure 29B:
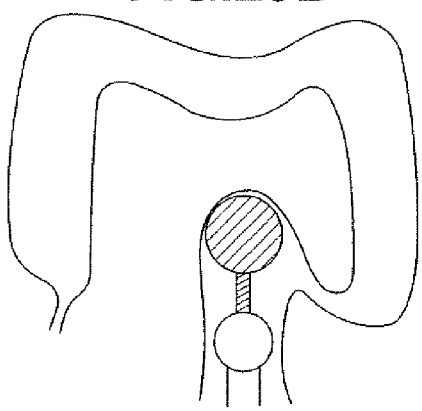
Figure 29C:
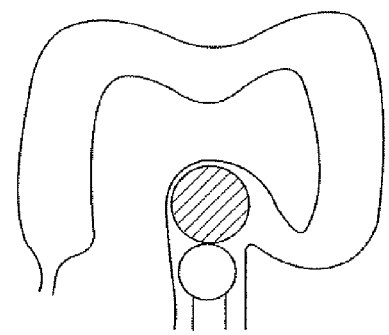
Figure 29D:
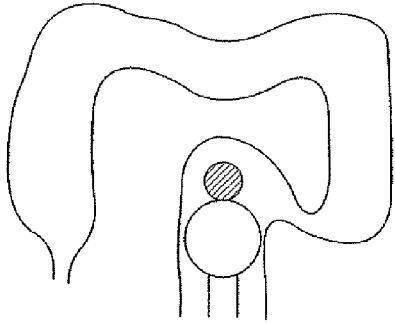
Figure 29E:
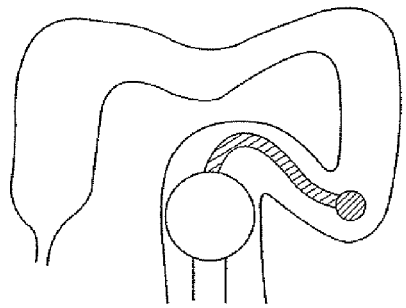
Figure 29F:
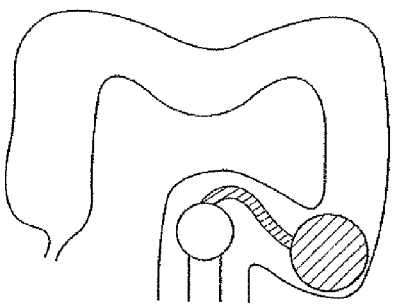
Figure 29G:
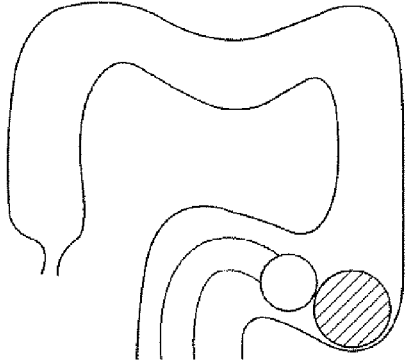
Figure 29H:
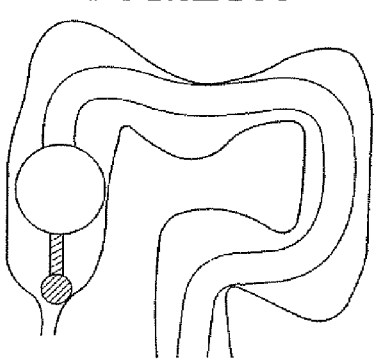

In this way, the distal end portions 21 and 22 of the two medical instruments 2a and 2b can advance toward a deep intestinal portion by alternately achieving fixation to the intestinal wall 9 with the aid of the balloon portion 31 or 32. Then, as shown in FIG. 28G, at the point when the distal end portions 21 and 22 have advanced to some extent, the endoscope 2c is advanced toward a deeper intestinal portion.

In the apparatus for advancing an endoscope according to the present embodiment, neither of the medical instruments 2a and 2b has the endoscopic functions, and thus these medical instruments are the ones used only for the purpose of advancing the endoscope 2c to a deep intestinal portion. The medical instruments 2a and 2b, which are projected from the distal end portion of the endoscope 2c through forceps channels of the endoscope 2, may be removed from the forceps channels after the endoscope 2c has reached a targeted deep intestinal portion, so that other medical instruments can be inserted into the forceps channels.

The present invention is not limited to the embodiments and modifications described above, but may be variously changed and improved, for example, within the scope without changing the spirit of the present invention.

What is claimed is:

1. An apparatus for advancing an endoscope comprising:
   a first medical instrument comprising endoscopic functions and a second medical instrument comprising an over tube for the first medical instrument, wherein:
   each of the first medical instrument and the second medical instrument includes a fixing portion at a distal end portion thereof for fixation to an intestinal wall,
   the fixing portion provided at the first medical instrument is configured to form a gap in a state of being fixed to the intestinal wall, where the gap enables the distal end portion of the second medical instrument to advance therethrough, and
   the fixing portion provided at the second medical instrument is configured to form a gap in a state of being fixed to the intestinal wall, where the gap enables the distal end portion of the first medical instrument to advance therethrough.

2. The apparatus for advancing an endoscope according to claim 1, wherein the fixing portion of at least one of the first medical instrument and the second medical instrument is an inflatable/shrinkable balloon portion.

3. The apparatus for advancing an endoscope according to claim 1, wherein the fixing portion of at least one of the first medical instrument and the second medical instrument is an extensible mechanical member.

4. The apparatus for advancing an endoscope according to claim 1, the apparatus further comprising a retaining portion for retaining an inter-axis distance between the first medical instrument and the second medical instrument.

5. The apparatus for advancing an endoscope according to claim 4, wherein:
   the fixing portion of each of the first medical instrument and the second medical instrument is a balloon portion comprising two balloons; and
   the retaining portion is a sheath covering and bundling substantially the entire length of the first medical instrument and the second medical instrument.

6. The apparatus for advancing an endoscope according to claim 5, the apparatus further comprising an advancement aiding member comprising:
   a first cable inserted through the first medical instrument, the ends of the first cable being connected to respective ends of the second medical instrument; and
   a second cable inserted through the second medical instrument, the ends of the second cable being connected to respective ends of the first medical instrument.

7. The apparatus for advancing an endoscope according to claim 1, the apparatus further comprising a stopper for adjusting sliding movement of the over tube.

8. The apparatus for advancing an endoscope according to claim 1, the apparatus further comprising:
   a notch portion formed at the distal end portion of the over tube, the notch portion being configured to receive the fixing portion provided at the first medical instrument of the second medical instrument as the second medical instrument is advanced relative to the first medical instrument.

9. The apparatus for advancing an endoscope according to claim 8, wherein a length of the notch portion in an axial direction of the over tube larger than a diameter of the fixing portion of the first medical instrument in an axial direction of the first medical instrument.

10. The apparatus for advancing an endoscope according to claim 1, wherein the fixing portion provided at the first medical instrument is configured to engage the intestinal wall in a first radial direction of the apparatus, and the fixing portion provided at the second medical instrument is configured to engage the intestinal wall in a second radial direction substantially orthogonal to the first radial direction.

11. A method for manipulating an apparatus for advancing an endoscope, wherein the apparatus includes:

a first medical instrument comprising endoscopic functions and a second medical instrument comprising an over tube for the first medical instrument, wherein:
    each of the first medical instrument and the second medical instrument includes a fixing portion at a distal end portion thereof for fixation to an intestinal wall,
    the fixing portion provided at the first medical instrument is configured to form a gap in a state of being fixed to the intestinal wall, where the gap enables the distal end portion of the second medical instrument to advance therethrough, and
    the fixing portion provided at the second medical instrument is configured to form a gap in a state of being fixed to the intestinal wall, where the gap enables the distal end portion of the first medical instrument to advance therethrough, the method comprising reiteration of:
    a fixing manipulation for fixing one of the first medical instrument and the second medical instrument to an intestinal wall;
    an advancing manipulation for advancing a distal end portion of the other of the first medical instrument and the second medical instrument, which is not fixed to the intestinal wall, to a deeper portion than a fixing spot where the fixed medical instrument is fixed to the intestinal wall; and
    a fixing manipulation for fixing the distal end portion of the other of the first medical instrument and the second medical instrument to the intestinal wall, so that all the medical instruments can be fixed to the intestinal wall, the method further comprising reiteration of:
    a fixation releasing manipulation for releasing fixation of the medical instrument fixed to the intestinal wall in a shallowest portion from the intestinal wall;
    an advancing manipulation for advancing a distal end portion of the medical instrument released from fixation to a deeper portion than a fixing spot of the other medical instrument; and
    a fixing manipulation for fixing the medical instrument released from fixation to the intestinal wall.

12. A method for manipulating an apparatus for advancing an endoscope, wherein the apparatus includes:
    a first medical instrument comprising endoscopic functions and a second medical instrument comprising an over tube for the first medical instrument, wherein:
    each of the first medical instrument and the second medical instrument includes a fixing portion at a distal end portion thereof for fixation to an intestinal wall,
    the fixing portion provided at the first medical instrument is configured to form a gap in a state of being fixed to the intestinal wall, where the gap enables the distal end portion of the second medical instrument to advance therethrough, and
    the fixing portion provided at the second medical instrument is configured to form a gap in a state of being fixed to the intestinal wall, where the gap enables the distal end portion of the first medical instrument to advance therethrough, the method comprising sequential reiteration of:
    a fixing manipulation for operating the fixing portion of the first medical instrument to fix the first medical instrument to a first fixing spot of the intestinal wall;
    an advancing manipulation for advancing a distal end portion of the second medical instrument to a deeper portion than the fixing spot of the first medical instrument;
    a fixing manipulation for operating the fixing portion of the second medical instrument to fix the second medical instrument to a second fixing spot of the intestinal wall;
    a fixation releasing manipulation for operating the fixing portion of the first medical instrument to release fixation between the first medical instrument and the intestinal wall; and
    an advancing manipulation for advancing a distal end portion of the first medical instrument to a deeper portion than the second fixing spot of the second medical instrument.

13. The method for manipulating the apparatus for advancing an endoscope according to claim 12, wherein the apparatus further includes an advancement aiding member comprising:
    a first cable inserted through the first medical instrument, the ends of the first cable being connected to respective ends of the second medical instrument; and
    a second cable inserted through the second medical instrument, the ends of the second cable being connected to respective ends of the first medical instrument, the method further comprising: is used to
    sequentially pull the first cable and the second cable.

\* \* \* \* \*